United States Patent
Miller

(10) Patent No.: US 8,007,468 B2
(45) Date of Patent: Aug. 30, 2011

(54) METHOD TO SECURE AN ELASTIC COMPONENT IN A VALVE

(75) Inventor: Stephen C. Miller, Queensbury, NY (US)

(73) Assignee: Navilyst Medical, Inc., Marlborough, MA (US)

(*) Notice: Subject to any disclaimer, the term of this patent is extended or adjusted under 35 U.S.C. 154(b) by 0 days.

(21) Appl. No.: 12/501,809

(22) Filed: Jul. 13, 2009

(65) Prior Publication Data

US 2011/0009811 A1    Jan. 13, 2011

(51) Int. Cl.
*A61M 1/00* (2006.01)
(52) U.S. Cl. ............................................. 604/118
(58) Field of Classification Search ............... 604/247, 604/256, 118; 251/30.02, 30.05, 149, 335.1, 251/355.2; 222/490
See application file for complete search history.

(56) References Cited

U.S. PATENT DOCUMENTS

| | | | |
|---|---|---|---|
| 3,669,323 A * | 6/1972 | Harker et al. | 222/490 |
| 5,484,420 A | 1/1996 | Russo | |
| 2002/0193752 A1 | 12/2002 | Lynn | |
| 2005/0049555 A1 * | 3/2005 | Moorehead et al. | 604/122 |
| 2006/0135949 A1 | 6/2006 | Rome et al. | |
| 2008/0108956 A1 * | 5/2008 | Lynn et al. | 604/256 |

OTHER PUBLICATIONS

PCT International Search Report (Form PCT/ISA/210) for International Application No. PCT/US2010/041698 mailed Sep. 3, 2010.

* cited by examiner

*Primary Examiner* — Theodore J Stigell
*Assistant Examiner* — Deanna K Hall
(74) *Attorney, Agent, or Firm* — Bingham McCutchen LLP

(57) ABSTRACT

An apparatus for controlling fluid flow through medical devices, specifically for sealing devices which remain in place in the body to provide long term access to the vascular system. Exemplary embodiments of the present invention describe a wedge or other similarly shaped geometrical feature for fixing an elastic component and controlling an internal stress of the elastic component.

16 Claims, 2 Drawing Sheets

METHOD TO SECURE AN ELASTIC COMPONENT IN A VALVE

BACKGROUND

Pressure activated safety valves have been incorporated into medical devices such as peripherally inserted central catheters (PICCs), ports, dialysis catheters and tunneled central catheters which provide long term access to the vascular system, etc. These valves generally include an elastic component that controls flow and/or pressure through the device to prevent flow therethrough when the device is not in use. The elastic component may be a slitted, flexible membrane extending across a lumen generally constructed so that, when subjected to a fluid pressure of at least a threshold magnitude, edges of the slit separate from one another to permit flow through the lumen. When the pressure applied to the membrane drops below the threshold level, the slit reseals to prevent leakage from or into the device. It is desirable to keep the flexible disk in place during high pressure and/or flow while maintaining the desired flow control characteristics of the membrane.

SUMMARY OF THE INVENTION

The present invention is directed to a valve comprising a flexible member including a slit formed on a central portion thereof and a first housing defining a first lumen extending therethrough, the first housing including a first contacting surface adapted, when the slit of the flexible member is aligned with the first lumen, to contact a first side of the flexible member the first housing defining a relief area extending about a perimeter of the first contacting surface radially outside the central portion relative to a longitudinal axis of the first lumen in combination with a second housing adapted to mate with the first housing with a second lumen defined by the second housing aligned with the first lumen and separated therefrom by the flexible member, the second housing including a second contacting surface which, when the first and second housings are mated to one another in an operative configuration with the flexible member pinched therebetween, contacts a second side of the flexible member opposite the first side thereof along the longitudinal axis, a radially outer portion of the second contacting surface including a protrusion aligning with and extending into the relief area when the first and second housings are mated in the operative configuration, the protrusion bending a peripheral portion of the flexible member about a radially outer edge of the first contacting surface into the relief area to maintain the flexible member at a desired position separating the first and second lumens so that, when subject to a fluid pressure of at least a predetermined magnitude, the slit of the flexible member opens to permit fluid transfer between the first and second lumens and, when subject to a fluid pressure less than the predetermined magnitude, the slit of the flexible member remains closed preventing fluid transfer between the first and second lumens.

DETAILED DESCRIPTION

Figure 1:
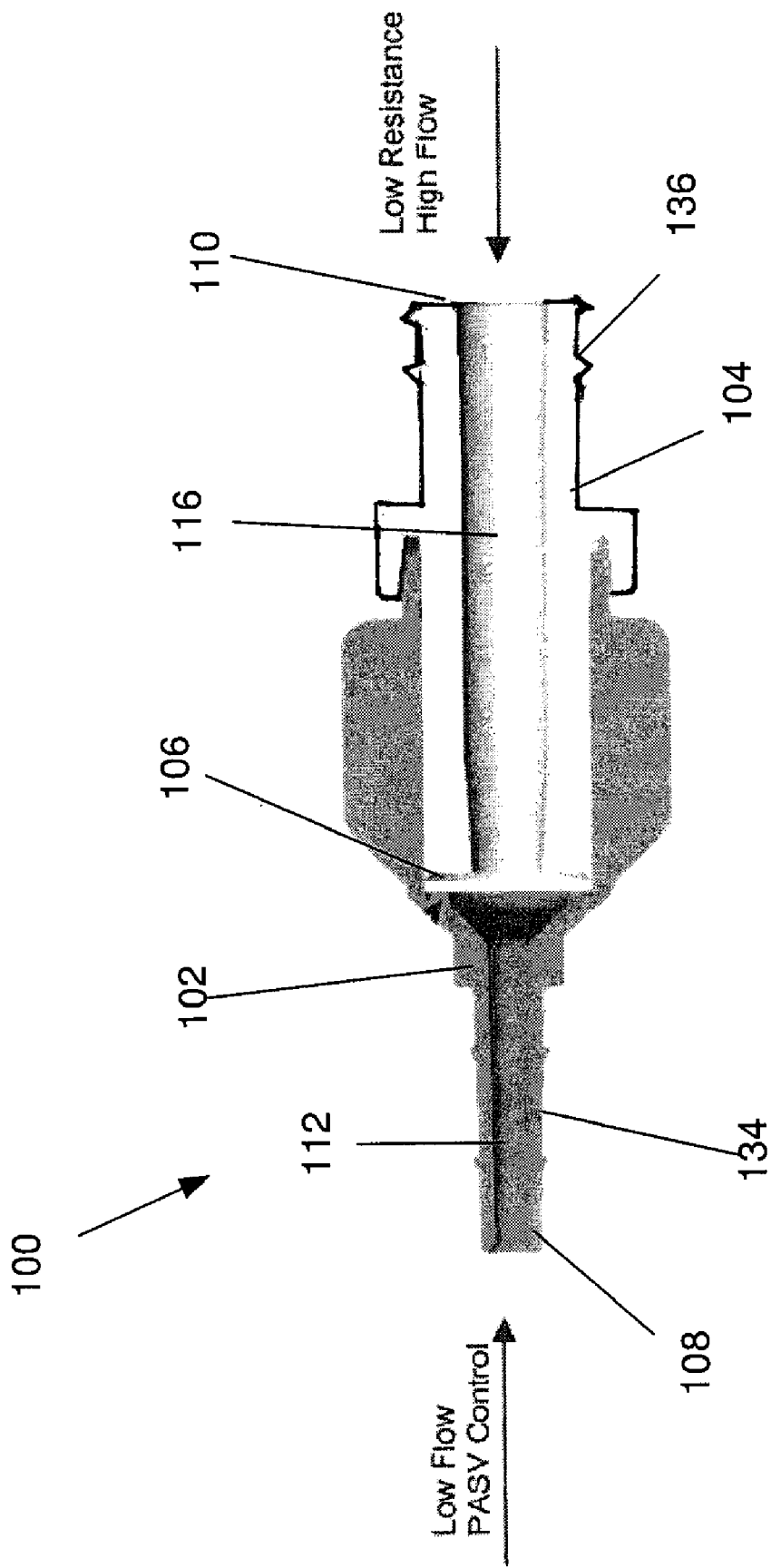
FIG. 1 shows a longitudinal cross-sectional view of a device according to an exemplary embodiment of the present invention.

The present invention may be further understood with reference to the following description and the appended drawings, wherein like elements are referred to with the same reference numerals. The present invention relates to an apparatus for controlling fluid flow through medical devices specifically for sealing devices which remain in place in the body to provide long term access to the vascular system. To improve the performance of pressure activated safety valves, exemplary embodiments of the present invention describe a wedge or other similarly shaped geometrical feature for fixing an elastic component and controlling an internal stress of the elastic component.

Figures 2, 3:
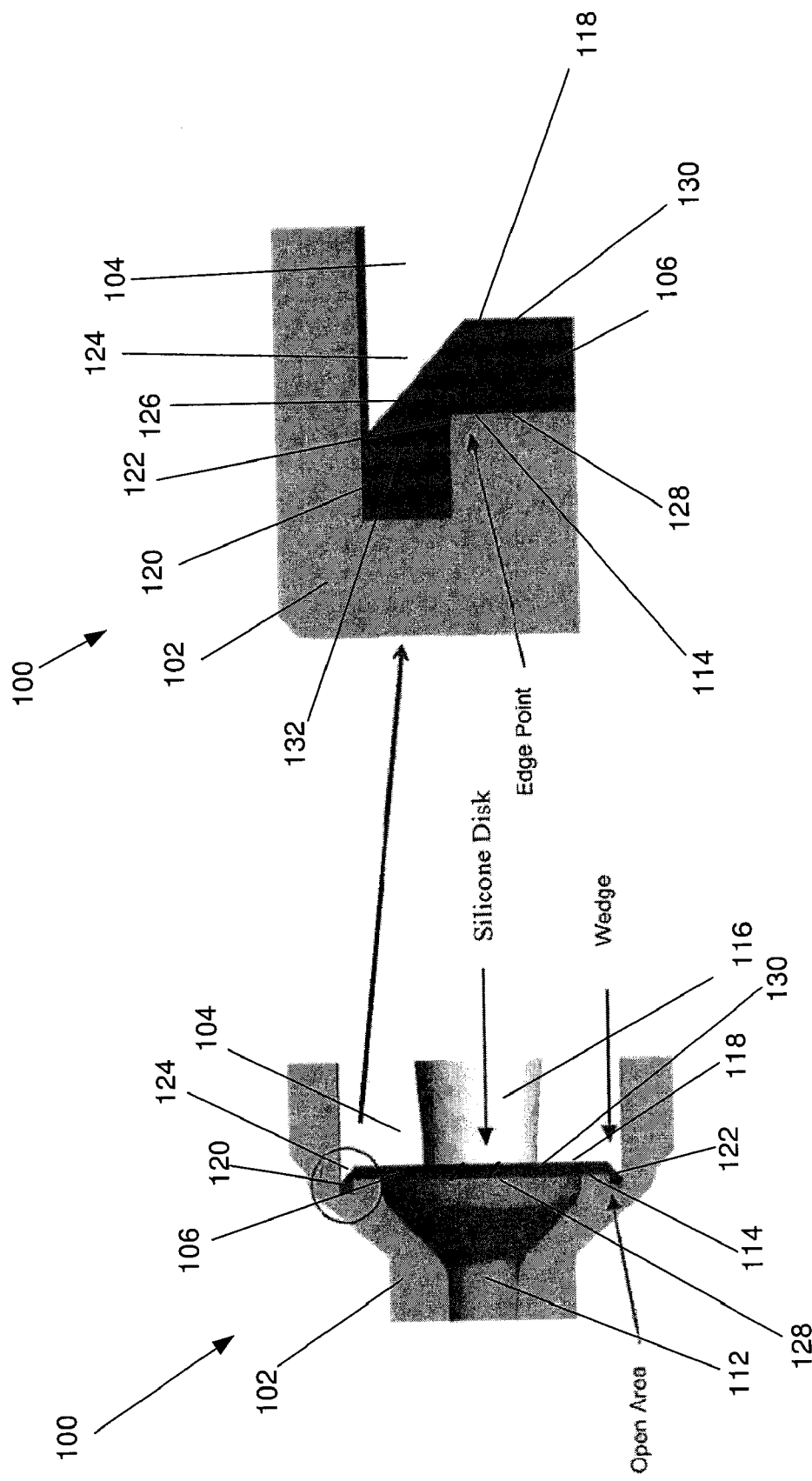
FIG. 2 shows a longitudinal cross-sectional view of a disk portion of the device of FIG. 1.
FIG. 3 shows an enlarged view of portion of an edge of the disk portion of the device shown in FIG. 2.

As shown in FIGS. 1-3, a device 100 according to an exemplary embodiment of the present invention comprises a first housing 102, a second housing 104 and an elastic component 106. As shown in FIG. 1, the first housing 102 and the second housing 104 maybe coupled to one another to fix the elastic component 106 therebetween. For clarity, the elastic component 106 is shown between the first and the second housings 102, 104 before being pinched into the final position. The first housing 102 may form a distal end 108 of the device 100 and includes a first connection 134 for connecting to a first conduit which extends, for example, to a target body structure to and/or from which it is desired to transfer fluids. The second housing 104, at a proximal end 110 of the device 100, includes a second connection 136 for connecting to a second conduit which remains external to the body. The elastic component 106 is fixed between the first and the second housings 102, 104 to control a fluid flow therethrough.

The elastic component 106 may be any flexible membrane (e.g., in the form of a disk) including a slit (not shown) for controlling fluid flow therethrough such as, for example, a silicone disk. The elastic component 106 may operate as a bi-directional valve allowing fluid to flow through the device 100 in either direction whenever the valve is subjected to a fluid pressure of at least a threshold value. Alternatively, the elastic component 106 may operate as a unidirectional valve allowing fluid to flow in only one direction or having different threshold values for each of the two directions of flow therethrough. The elastic component 106 is configured to open only when fluid pressure exerted thereagainst reaches a predetermined threshold magnitude. The slit opens via a deformation of the elastic component 106 with edges of the slit moving away from one another to allow fluid to flow therethrough. Once fluid pressure falls below the threshold magnitude, the slit reseals preventing fluid from flowing therethrough. It will be understood by those of skill in the art that the elastic component 106 may include more than one slit extending therethrough.

As shown in FIGS. 2-3, the first housing 102 includes a lumen 112 extending therethrough and a disk-facing surface 114, which contacts the elastic component 106. The disk-facing surface 114 includes a substantially planar central portion 128 surrounding the lumen 112 and a relief area 120 radially outside the planar central portion 128 (relative to a longitudinal axis of the first and second housings 102, 104). The relief area 120 may be formed as a recess extending around a radially outer edge of the disk-facing surface 114 for accommodating an outer perimeter 132 of the elastic component 106. The relief area 120 further includes an edge 122 over which the outer perimeter 132 of the elastic component 106 may be bent. It will be understood by those of skill in the art that the relief area 120 may be formed as either a continuous recess about the perimeter of the disk-facing surface 114 or as a series of recesses spaced from one another around the circumference of the disk-facing surface 114. In a preferred embodiment, the relief area 120 forms a ring-shaped recess about a circumference of the disk-facing surface 114.

The second housing 104 includes a lumen 116 extending therethrough and a disk-facing surface 118, which contacts the elastic component 106. The disk-facing surface 118 includes a substantially planar central portion 130 surrounding the lumen 116 and a protrusion 124 surrounding the planar central portion 130. The protrusion 124 extends distally away from the planar central portion 130 around a radially outer edge of the disk-facing surface 118. The protrusion 124 may be, for example, wedge-shaped including an angled surface 126 which contacts a radially outer portion of the elastic component 106 bending it over the edge 122 distally into the relief area 120. It will be understood by those of skill in the art that the protrusion 124 may extend continuously about the outer perimeter of the disk-facing surface 118 or may be formed as a series of protrusions separated from one another circumferentially about the outer perimeter of the disk-facing surface 118 by a series of recesses or gaps. In a preferred embodiment, the protrusion 124 is substantially ring-shaped and extends continuously around a circumference of the disk-facing surface 118.

The relief area 120 and the protrusion 124 of the first and the second housings 102, 104, respectively, enhance retention of the elastic component 106 applying compression to the elastic component 106 radially inward toward the longitudinal axis of the first and second housings 102, 104, respectively, to counteract tension to which the elastic component 106 is subjected as it is pinched between the first and second housings 102, 104 and stretched into the relief area 120. Initially, as the elastic component 106 is being pinched between the first and second housings 102, 104, as the outer edge of the elastic component 106 is bent around the edge 122 into the relief area 120, the central portion of the elastic component 106 is stretched radially outward drawing edges of the slit away from one another and puckering the central portion of the elastic component. Then, as the first and second housings 102, 104 are moved further toward one another, the elastic component 106 is pinched between the protrusion 124 and the edge 122 reducing a thickness of this portion of the elastic component 106 and urging the material pinched away from this area toward the slit—i.e., compressing the elastic component 106 radially to bring the edges of the slit back together sealing the valve. The planar portion 130 of the disk-facing surface 118 keeps the central portion of the elastic component 106 substantially flat so that the elastic component 106 does not pucker, aligning edges of the slit while under compression. In addition, the bending of the peripherally outer portion of the elastic component 106 over the edge 122 into the relief area 120 reduces the likelihood that the elastic component 106 will be pulled out of position between the first and second housings 102, 104 when subjected to excess pressure. That is, the outer perimeter 132 of the elastic component 106 extends radially outward of the edge 122 in the relief area 120 with the outer perimeter 132 acting as an anchor holding the elastic component 106 in place.

It will be understood by those of skill in the art that the compression force for closing the slit may be controlled by altering the angle of the angled surface 126 and a position of the protrusion 124 in relation to the edge 122. In a preferred embodiment, the angled surface 126 may be angled from between approximately 40E to 50E and more preferably, at an angle of approximately 45E. The location of the edge 122 may be determined by the angled surface 126, which is positioned to the periphery of the flexible member 106. Thus, the compression force may be controlled as desired. It will also be understood by those of skill in the art that the amount of compression on the slit and/or the elastic component 106 is one of the factors determining the pressure gradients needed to open and close the slit. Other factors may include, for example, a flexibility, a thickness, and a material of the elastic component 106.

It will be apparent to those skilled in the art that various modifications and variations may be made in the structure and the methodology of the present invention, without departing from the spirit or scope of the invention. Thus, it is intended that the present invention cover the modifications and variations of this invention provided that they come within the scope of the appended claims and their equivalents.

What is claimed is:

1. A valve for controlling a flow of liquid through a conduit extending between an internal structure within a living body and an exterior of the living body, comprising:
    a flexible member, including a slit formed on a central portion thereof, that is designed to act accordingly to a predetermined fluid pressure;
    a first housing defining a first lumen extending therethrough, the first housing including a first contacting surface adapted to contact a first side of the flexible member, the first housing defining a relief area extending about a perimeter of the first contacting surface; and
    a second housing adapted to mate with the first housing, the second housing defining a second lumen and separated from the first housing by the flexible member, the second housing including a second contacting surface which, when the first and second housings are mated to one another in an operative configuration with the flexible member located there between, contacts a second side of the flexible member, a radially outer portion of the second contacting surface including a substantially wedge-shaped protrusion that aligns with and extends into the relief area when the first and second housings are mated in the operative configuration, the protrusion contacting the flexible member such that a peripheral portion of the flexible member extends into the relief area, and wherein the protrusion extends substantially and continuously around a perimeter of the second contacting surface.

2. The valve of claim 1, wherein a portion of the contacting surface radially within the protrusion is substantially planar and extends annularly about the second lumen.

3. The valve of claim 1, wherein the first and second housings are adapted, when mated in the operative configuration, to compress the flexible member toward the longitudinal axis in an amount corresponding to a radially outward tension applied to the flexible member by the bending of the peripheral portion into the relief area.

4. The valve of claim 3, wherein the first contacting surface is formed as a substantially planar annular area surrounding the first lumen, the first and second contacting surfaces maintaining the first and second surfaces of the flexible member substantially planar.

5. The valve of claim 1, wherein the predetermined pressure is selected to be above the pressures to which the valve will be subjected due to natural fluctuations in a fluid pressure within a target body structure to which it is to be fluidly coupled.

6. The valve of claim 1, wherein the flexible member is formed as a disk-shaped membrane, the material of which the flexible member is formed being biased to close the slit when subjected to a fluid pressure less than the predetermined fluid pressure.

7. The valve of claim 1, wherein the flexible member has a first predetermined pressure for flow therethrough from a proximal side to a distal side thereof and a second predetermined pressure different from the first predetermined pressure for flow therethrough from a distal side to a proximal side thereof.

8. The valve of claim 1, wherein the flexible member includes two slits extending therethrough.

9. A valve for controlling a flow of liquid through a conduit extending between an internal structure within a living body and an exterior of the living body, comprising:
 a flexible member, including a slit formed on a central portion thereof, that is designed to act accordingly to a predetermined fluid pressure;
 a first housing defining a first lumen extending therethrough, the first housing including a first contacting surface adapted to contact a first side of the flexible member, the first housing defining a relief area extending about a perimeter of the first contacting surface; and
 a second housing adapted to mate with the first housing, the second housing defining a second lumen and separated from the first housing by the flexible member, the second housing including a second contacting surface which, when the first and second housings are mated to one another in an operative configuration with the flexible member located there between, contacts a second side of the flexible member, a radially outer portion of the second contacting surface including a protrusion that aligns with and extends into the relief area when the first and second housings are mated in the operative configuration, the protrusion contacting the flexible member such that a peripheral portion of the flexible member extends into the relief area,
  wherein the protrusion is formed as a series of discontinuous raised areas separated circumferentially from one another by gaps around the perimeter of the second contacting surface, and
  wherein the protrusion extends substantially and continuously around a perimeter of the second contacting surface.

10. The valve of claim 9, wherein a portion of the contacting surface radially within the protrusion is substantially planar and extends annularly about the second lumen.

11. The valve of claim 9, wherein the first and second housings are adapted, when mated in the operative configuration, to compress the flexible member toward the longitudinal axis in an amount corresponding to a radially outward tension applied to the flexible member by the bending of the peripheral portion into the relief area.

12. The valve of claim 11, wherein the first contacting surface is formed as a substantially planar annular area surrounding the first lumen, the first and second contacting surfaces maintaining the first and second surfaces of the flexible member substantially planar.

13. The valve of claim 9, wherein the predetermined pressure is selected to be above the pressures to which the valve will be subjected due to natural fluctuations in a fluid pressure within a target body structure to which it is to be fluidly coupled.

14. The valve of claim 9, wherein the flexible member is formed as a disk-shaped membrane, the material of which the flexible member is formed being biased to close the slit when subjected to a fluid pressure less than the predetermined fluid pressure.

15. The valve of claim 9, wherein the flexible member has a first predetermined pressure for flow therethrough from a proximal side to a distal side thereof and a second predetermined pressure different from the first predetermined pressure for flow therethrough from a distal side to a proximal side thereof.

16. The valve of claim 9, wherein the flexible member includes two slits extending therethrough.

* * * * *